United States Patent [19]

Poole et al.

[11] 4,442,088

[45] Apr. 10, 1984

[54] TUMOR ENZYME DETECTION

[75] Inventors: A. Robin Poole, Baie d' Urfe; John S. Mort; Anneliese D. Recklies, both of Point Claire, Canada

[73] Assignee: Shriners Hospitals for Crippled Children, Tampa, Fla.

[21] Appl. No.: 307,085

[22] Filed: Sep. 29, 1981

[51] Int. Cl.³ .............................................. A61K 39/00
[52] U.S. Cl. .................................... 424/85; 424/101; 436/547
[58] Field of Search .................. 424/85, 101; 536/547; 260/112 R, 112 B

[56] References Cited

PUBLICATIONS

Barrett, A., "Cathepsin B and Other Thiol Proteinases", Proteinases in the Mammalian Cells and Tissues, pp. 181-208, (1977).
Chemical Abstracts, vol. 94, p. 437, Abst. No. 171637h, 1981.
Chemical Abstracts, vol. 89, p. 441, Abst. No. 144790t, 1978.
Mort et al., The Journal of Histochemistry and Cytochemistry, vol. 29, pp. 649-657, 1981.
Poole et al., Arthritis and Rheumatism, vol. 19, pp. 1295-1307, 1976.
Poole et al., Nature, vol. 273, pp. 545-547, 1978.
Recklies et al., Cancer Research, vol. 40, pp. 550-556, 1980.
Mort et al., Biochimica et Biophysica Acta, vol. 614, pp. 134-143, 1980.
Poole et al., *Proteinases and Tumor Invasion*, pp. 81-95, 1980.
Bansal et al., Acta Diabet. Lat., vol. 17, pp. 255-266, 1980.
Pierart-Gallois et al., Acta Biol. Med. Germ., vol. 36, pp. 1887-1891, 1977.
Sylven et al., Histochemistry, vol. 38, p. 35, 1974.
Sylven et al., Virch, Arch. B. Cell Pathol, vol. 17, p. 97, 1974.

*Primary Examiner*—Blondel Hazel
*Attorney, Agent, or Firm*—Schroeder, Siegfried, Vidas & Arrett

[57] ABSTRACT

A monospecific antibody prepared in response to cathepsin B proteinase by homogenizing purified cathepsin B proteinase upon dialyzing to remove ampholines, injecting a proteinase emulsion intramuscularly into an animal, reinjecting the animal with the proteinase emulsion, with drawing blood of the animal after sufficient time elapse for antibody production and isolating the monospecific antiserum from the blood.

6 Claims, No Drawings

TUMOR ENZYME DETECTION

FIELD OF THE INVENTION

This invention relates to the production, purification and use of antibodies specific to enzymes which may be indicators of cancer involvement. In particular, the enzymes belong to the class called thiol proteinases.

BACKGROUND OF THE INVENTION

The distinguishing features of malignant disease are the capacity of tumors for uncontrolled growth, local invasion of host tissue and dissemination of tumor cells into the circulatory system. The action of proteolytic enzymes has been implicated in many of the events leading to the development of extensive malignant disease. Degradation of connective tissue and basement membrane components are instrumental in the local spread of tumor cells, as well as in their migration into and out of the circulatory system.

Lysosomal enzyme cathepsin B is a thiol proteinase present in most, if not all animal tissues. Thiol proteinase secretions have been seen in primary malignant breast tumors and metastases for patients with previous breast carcinomas. In order to follow-up this possible link between thiol proteinases and cancer activity, assays were developed for thiol proteinases. However, since more than one proteinase can degrade the same synthetic substrate, a less specific demonstration of a particular proteinase is achieved than by immunological methods. Antiserum to the thiol proteinase cathepsin B has been raised but no data was published regarding the specificity of the antiserum. See Barrett, A. J., "Cathepsin B and Other Thiol Proteinases," In *Proteinases In Mammalian Cells and Tissues*. (1977) In order to be useful as a diagnostic or locational tool, antiserum to cathepsin B must be completely specific as an absolute requirement. An article describing the preparation and characterization of a monospecific antiserum to human cathepsin B was published in 1981, by Poole, Mort and Decker in *The Journal of Histochemistry and Cytochemistry*, entitled "Immunofluorescent Localization of Cathepsin B and D in Human Fibroblasts," Vol. 29, No. 5, pp. 649-657.

BRIEF SUMMARY OF THE INVENTION

Monospecific antisera are provided to normal and tumor cathepsin B proteinases by injecting a purified proteinase into an animal. The animal's body then produces antiserum to the proteinase which is removed from the blood and highly purified. Once an antiserum is available that reacts with only one specific antigen, the proteinase first injected, the antiserum is used to determine the presence and amount of the proteinase in tissue samples or sera of a patient.

One object of the present invention is to raise purified specific antisera to cathepsin B and cathepsin B-like proteinases.

Another object is to provide an immunoassay for the determination of proteinases in serum with greater specificity than activity assays.

Still another object is to provide a process to raise monospecific antiserum to the tumor cathepsin B proteinase which may then be used to detect tumors in patients.

DETAILED DESCRIPTION OF THE INVENTION

In order to prepare monospecific antiserum, the antigen, which is the enzyme, must be highly purified. Cathepsin B is a thiol proteinase found in most animal tissues, No. EC3.4.22.1 in the *Enzyme Nomenclature List*, (1972) with a molecular weight of about 28,000. It is purified from human liver following a modification of the method of Barrett, A. J. in "Cathepsin B and other Thiol Proteinases" in *Proteinases in the Mammalian Cells and Tissues*, pages 181-208, (1977).

Cathepsin B is extracted from human liver tissue at pH 6.5. The removal of particulate material is facilitated by the use of a cationic detergent, under the trademark ARQUAD 2C-50 of Armour Industrial Chemical Co. of Chicago, Ill., but this is not essential, and high speed centrifugation may be employed instead. The supernatant is subjected to autolysis at pH 4.5 and 40° C. overnight. Fractionation in cold acetone is then employed.

The Cathepsin B is further purified by an ion-exchange stepwise elution on CM-cellulose. Cathepsin B is then eluted from an organomercurial-sepharose absorbent by a thiol reagent of cysteine or dithioerythritol.

Gel chromatography with Ultrogel AcA54 immediately follows the absorption step to remove the thiol, since thiol decreases the stability of the enzyme. After the gel filtration step, the substantially pure enzyme was subjected to preparative isoelectric focusing in a Sephadex G-75 superfine flat bed using a 2 percent pH 4-6 ampholine (BioRad) gradient.

The cathepsin B, 0.5 mg in 3 ml is dialyzed against 50 mM sodium acetate, 200 mM NaCl and 1 mM Ethylenediamino tetraacetate, hereinafter EDTA at a pH of 5.5 to remove ampholines and then homogenized for 15 seconds with 5 ml Freund's complete adjuvant using a Tissuizer homogenizer. The emulsion is injected intramuscularly into a sheep at four sites. After two weeks, a further 0.25 mg of enzyme in 1.5 ml of buffer emulsified with 2.5 ml of Freund's complete adjuvant is injected as before. The animal is bled out by intracarotid catheterization after a further 11 days. Monospecific antiserum or antibody to cathepsin B may then be isolated from the animal's blood by any of a number of well known techniques. One technique of purifying the antibody is described by Poole et al, in Arthritis Rheum 19:1295, (1976).

The specificity of the antiserum produced is demonstrated by the formation, on double immunodiffusion, of single precipitin lines with pure cathepsin B and crude human liver homogenate that show a reaction of the identity. That the antiserum gave no precipitin line at pH 6.5 against liver homogenate is also an indication of monospecificity. On crossed immunoelectrophoresis (migration in both dimensions taking place at pH 8.3) human liver homogenate gave a single rocket. This antiserum reacts only with denatured enzyme, thus, on double immonodiffusion a precipitin line will form only if cathepsin B is denatured.

A related cathepsin B-like proteinase has been found in human malignant tumors with a molecular weight of about 36,000 and an alkaline pH stability unlike normal cathepsin B. Monospecific antiserum to this tumor thiol proteinase may be produced in the same method as described above.

While sheep may be used as described to produce the antiserum to human cathepsin B, other animals may be used. Antiserum to human cathepsin B is raised in a rabbit, and antiserum to rabbit cathepsin B as raised in sheep have been prepared following the procedures in this disclosure.

While the invention has been described with reference to various specific preferred embodiments thereof, it is to be appreciated that modifications and variations can be made without departing from the scope of the invention which is limited only as defined in the appended claims.

What is claimed is:

1. The process of producing a monospecific antiserum to cathepsin B proteinase secreted by malignant tumors comprising essentially the steps of:
   (a) producing a proteinase emulsion by homogenizing purified cathepsin B proteinase after dialyzing to remove ampholines, said cathepsin B proteinase having a molecular weight of about 36,000 and being stable under alkaline pH conditions;
   (b) injecting the proteinase emulsion intramuscularly into an animal;
   (c) reinjecting the animal with the proteinase emulsion;
   (d) withdrawing blood of the animal after sufficient time elapses for antibody production; and
   (e) isolating the monospecific antiserum from the blood.

2. The process of claim 1 wherein blood of the animal is withdrawn 11 days after the second injection of proteinase emulsion.

3. The process of claim 1 wherein the enzyme is dialyzed against 50 mM sodium acetate, 200 mM NaCL and 1 mM EDTA at pH 5.5.

4. The process of claim 1 wherein purified cathepsin B proteinase is further purified by isoelectric focusing in a Sephadex G-75 superfine flat bed with a 2 percent pH 4–6 ampholine (BioRad) gradient.

5. The process of claim 1 wherein the animal is reinjected with proteinase emulsion after two weeks.

6. The process of claim 1 wherein the proteinase is homogenized with an adjuvant.

* * * * *

UNITED STATES PATENT AND TRADEMARK OFFICE
CERTIFICATE OF CORRECTION

PATENT NO. : 4,442,088
DATED : April 10, 1984
INVENTOR(S) : A. Robin Poole, John S. Mort and Anneliese D. Recklies It is certified that error appears in the above-identified patent and that said Letters Patent are hereby corrected as shown below:

Column 3, line 1, after "cathepsin B", delete "is" and substitute --as--.

Signed and Sealed this

Fourteenth Day of August 1984

[SEAL]

Attest:

GERALD J. MOSSINGHOFF

Attesting Officer

Commissioner of Patents and Trademarks